United States Patent [19]  [11]  4,431,426
Groshong et al.  [45]  Feb. 14, 1984

[54] METHODS AND APPARATUS FOR INTRAVENOUS THERAPY AND HYPERALIMENTATION

[76] Inventors: Leroy E. Groshong, 6446 SW. Raab Rd.; Ronald J. Brawn, 5712 SW. 52nd, both of Portland, Oreg. 97221

[21] Appl. No.: 193,629

[22] Filed: Oct. 3, 1980

Related U.S. Application Data

[62] Division of Ser. No. 67,753, Aug. 20, 1979, Pat. No. 4,327,722.

[51] Int. Cl.³ ............................................. A61M 25/00
[52] U.S. Cl. ..................................... 604/280; 604/158; 604/164; 604/283; 604/272
[58] Field of Search ............... 128/214.4, 347–350 V, 128/158; 604/164–170, 280–283, 272

[56] References Cited

U.S. PATENT DOCUMENTS

| | | | |
|---|---|---|---|
| 2,393,003 | 1/1946 | Smith | 604/170 |
| 3,020,913 | 2/1962 | Heyer | 128/350 V |
| 3,128,769 | 4/1964 | Scislowicz | 128/348 |
| 3,630,198 | 12/1971 | Henkin | 604/170 |
| 3,633,579 | 1/1972 | Alley et al. | 128/214.4 |
| 3,633,585 | 1/1972 | McDonald | 128/348 |
| 3,885,561 | 5/1975 | Cami | 128/350 V |
| 3,890,970 | 6/1975 | Gullen | 604/170 |
| 3,993,080 | 11/1976 | Loseff | 128/350 R |
| 4,037,600 | 7/1977 | Poncy et al. | 128/348 X |
| 4,068,659 | 1/1978 | Moorehead | 128/214.4 |

FOREIGN PATENT DOCUMENTS 1064445 12/1953 France .................................. 128/214.4

*Primary Examiner*—Dalton L. Truluck
*Attorney, Agent, or Firm*—Klarquist, Sparkman, Campbell, Leigh & Whinston

[57] ABSTRACT

Methods and apparatus for short term and long term intravenous therapy including hyperalimentation are disclosed. The proximal end of a flexible catheter having a one way valve adjacent its proximal end is inserted through the skin of a patient and into a vein having a suitably large flow of blood therethrough. The distal end of the catheter has a threaded male coupler for connecting it to a flow reducing adaptor and thence to a source of intravenous solution. The solution flows by gravity through the catheter and into the vein. A passer which can be connected to the male coupler is provided for subcutaneously threading the catheter during long term catheter placement.

3 Claims, 19 Drawing Figures

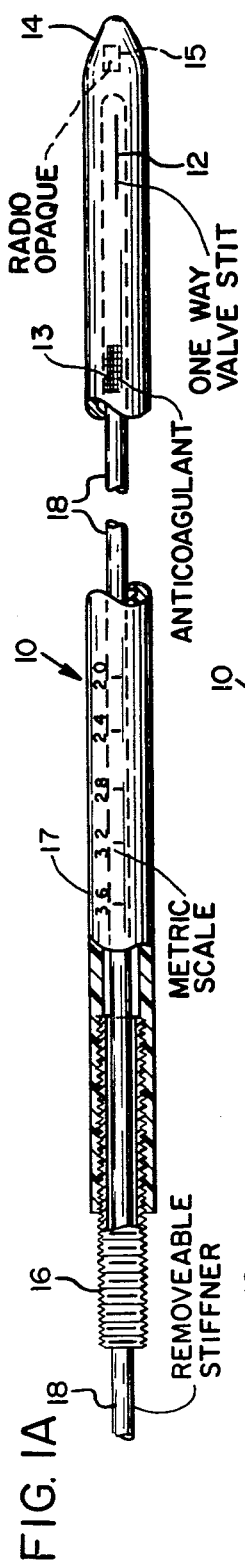
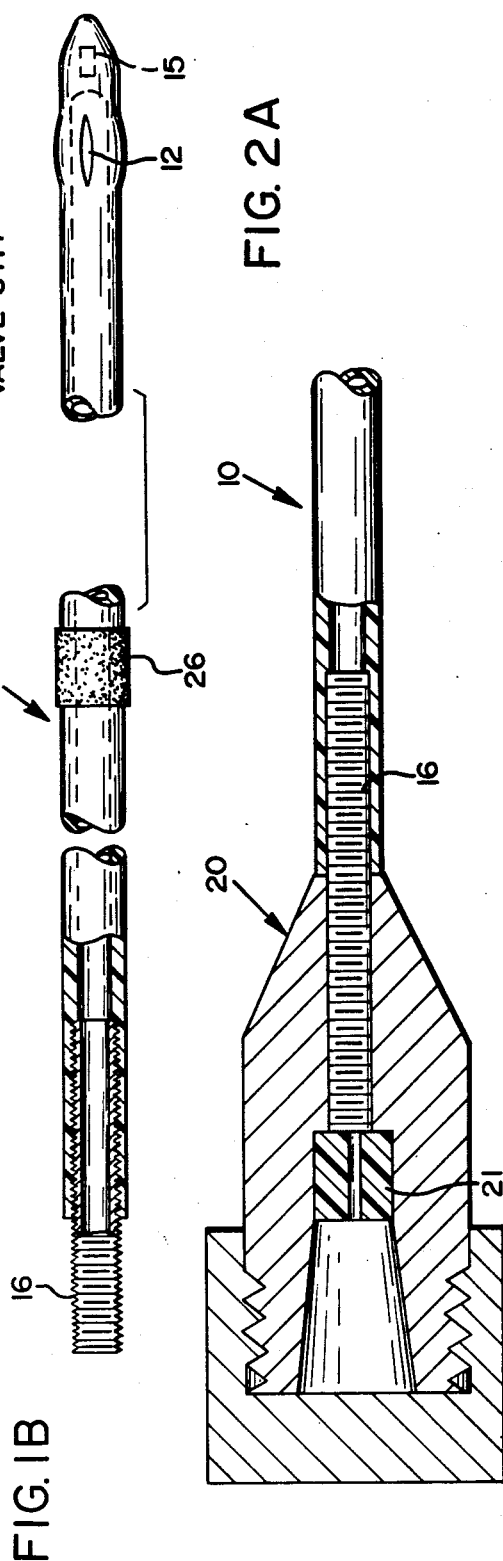
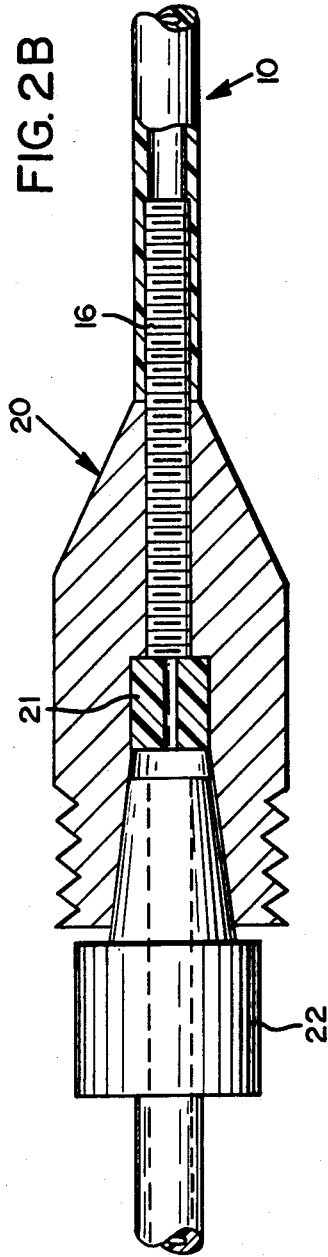

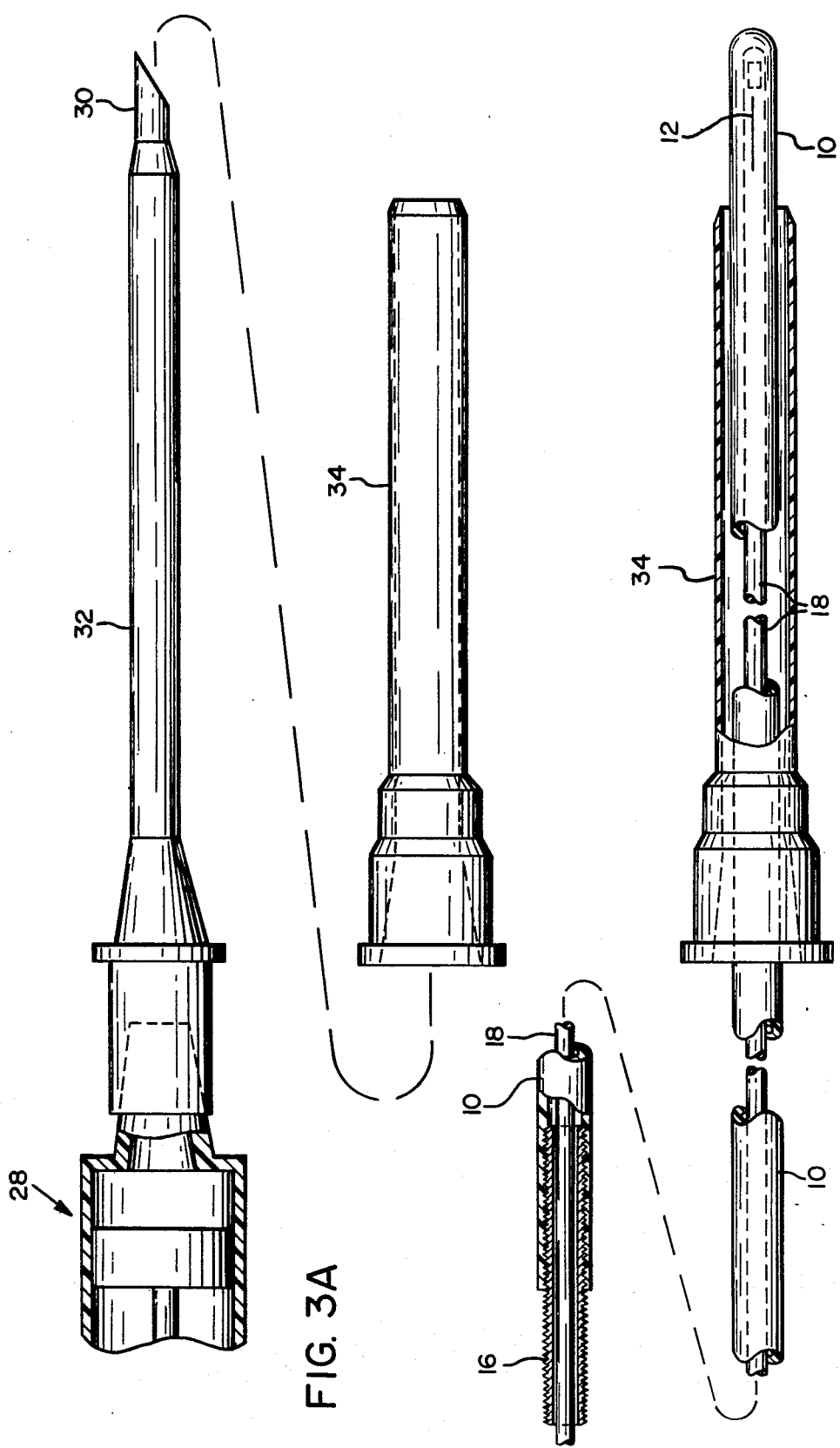

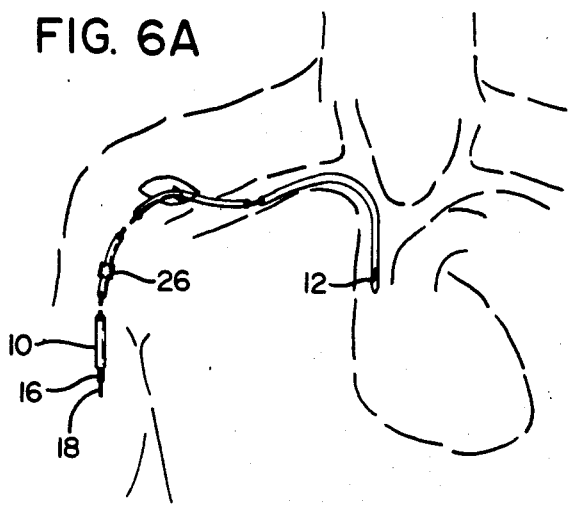
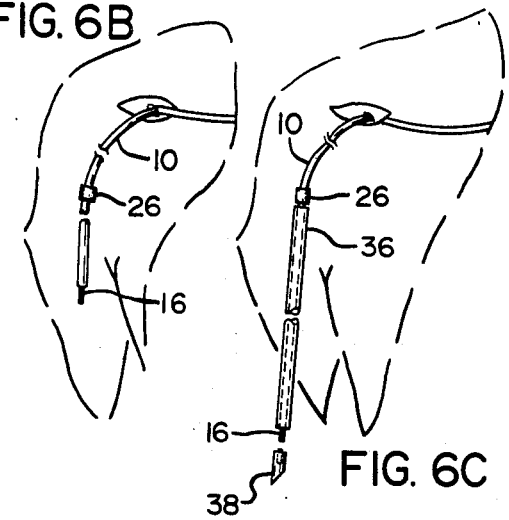
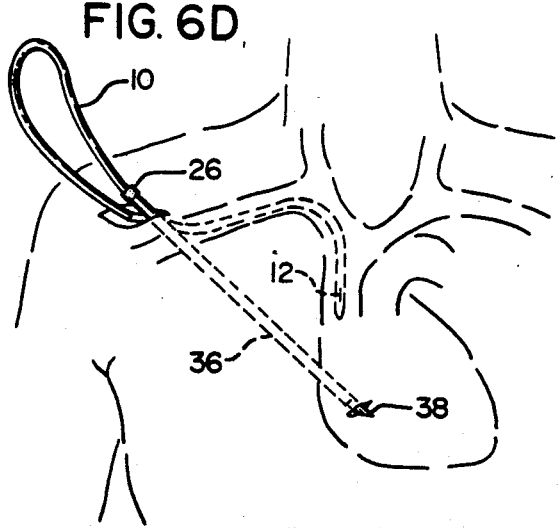
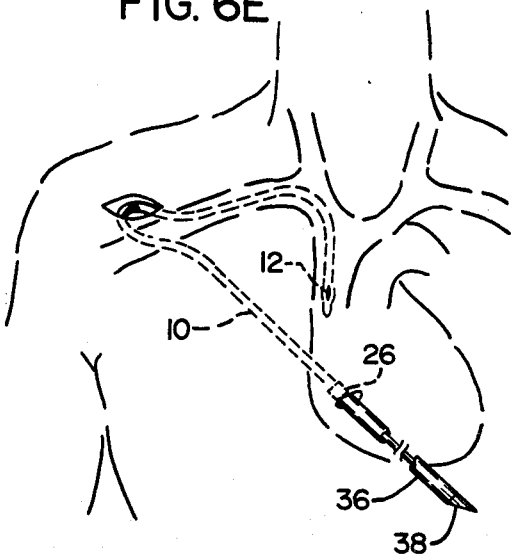
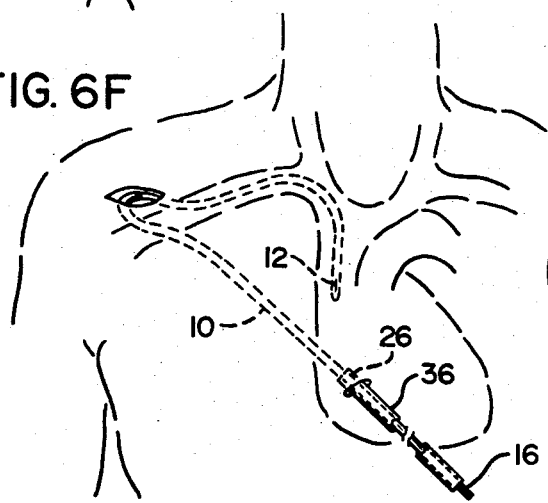
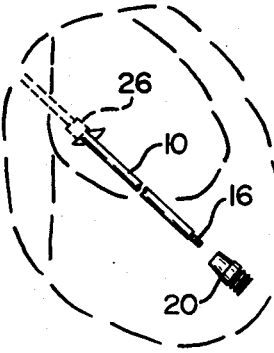
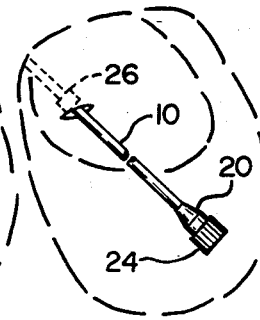

METHODS AND APPARATUS FOR INTRAVENOUS THERAPY AND HYPERALIMENTATION

This is a division of application Ser. No. 67,753, filed Aug. 20, 1979 now U.S. Pat. No. 4,327,722.

BACKGROUND OF THE INVENTION

The present invention relates to the intravenous administration of nutrients and therapeutic agents to patients and, more particularly, to methods and apparatus for administering intravenous hyperalimentation.

Ingestion, digestion, and absorption of food and assimilation of resulting substrates into the body cell mass are vital functions of the gastrointestinal tract. These functions may be impaired in a variety of ways. For example, infants born with gastrointestinal abnormalities, adults who develop gastrointestinal diseases, burn or accident victims, cancer patients, etc., may be unable to maintain their nutritional and fluid balance by oral intake. Without proper treatment they may die from starvation and dehydration.

Traditional intravenous feeding, i.e., through relatively small veins in the limbs, has severe limitations. A patient with one of the above described maladies may initially require eight liters or more of intravenous fluid per day with enough fats, proteins, and carbohydrates to meet the body's nutritional requirements and maintain positive nitrogen balance. Beyond three liters per day, however, the excess fluid strains the cardiovascular system. A diuretic may be given so that the kidneys can process the additional fluid. However, this method is dangerous.

Another approach is to increase the concentration of nutrients in the intravenous solutions. However, such solutions cannot be dripped into a relatively small vein in the arm or leg without severe pain coupled with the risk of vein inflammation and/or thrombosis.

In the early 1960's Dr. Stanley J. Dudrick and his colleagues developed a method of intravenous nutritional support (referred to in the medical profession as a hyperalimentation or total parenteral nutrition) by which normal growth and development as well as a positive nitrogen balance could be maintained. An open ended catheter was threaded through a moderate sized vein such as the subclavian, accessible under the collarbone, and into a very large vein, the superior vena cava. Because of the very large flow of blood through the superior vena cava a concentrated solution delivered through the catheter is rapidly diluted, thus allowing administration of a high concentration of nutrients without risk of pain, venous inflammation, or thrombosis.

Since Dr. Dudrick's initial work extensive research and development has been done with intravenous nutritional solutions. It has been possible to supply up to 7000 calories per day intravenously. Different apparatus and methods have evolved for short and long term intravenous therapy. With the latter, the distal end of the catheter is routed subcutaneously to an exit point midway down the anterior wall of the chest. The patient can then couple the catheter to a source of nutrients in the home and thus avoid prolonged hospitalization while still obtaining intensive intravenous nutritional therapy.

Serious problems heretofore encountered with hyperalimentation include potentially fatal air embolism which may occur when the distal end of the catheter becomes disconnected; severe or fatal hemorrhage which may also occur if the end of the catheter becomes disconnected; and blood reflux into the open proximal end of the catheter which may result in blood clots which interfere with and stop the flow of intravenous solution through the catheter. These clots may also form the nidus for bacterial or fungal growth which may then give rise to serious or fatal septicemias. If blood clots from the catheter enter the circulatory system the consequences may be serious or fatal. Therefore, it has been necessary to flush out the catheter with an anticoagulant as often as every four hours.

In order to avoid metabolic disorders due to excesses or deficiencies in the administrations of intravenous nutritional therapy it is necessary to control the amounts of nutrients and fluids supplied. Heretofore, every known apparatus for intravenous hyperalimentation has utilized costly pumps and flow sensing devices for controlling the rate of fluid administration, both to prevent too rapid administration which would result in severe metabolic disorders, and to prevent flow stoppage which may result in clotting in the catheter, making it unusable. A photoelectric sensor or some other device must be used to shut off the pump when the solution bottle has emptied otherwise a serious and possibly fatal air embolus will occur. If the pump is non-operative for just a short period of time, blood will reflux into the open proximal end of the catheter, causing a blood clot which may render the catheter inoperative or lead to other previously described complications.

Other problems involve the amount of hardware which must remain coupled to the distal end of the catheter after insertion. This inhibits the patient's mobility and increases the risk of accidental dislodgement, kinking, or cutting of the catheter. Furthermore, if intravenous therapy is temporarily suspended, the catheter must be flushed with an anticoagulant solution as frequently as every four hours to prevent blood clots from forming in the catheter. Finally, methods of passing the catheter through the subcutaneous tissue for permanent placement have been cumbersome and require separate tunnelling and threading procedures.

Catheters with one way valves adjacent their closed proximal ends have been used to deliver cerebrospinal fluid to the atrium of the heart. However, catheters with proximal one way valves have not heretofore been utilized to accomplish intravenous administration of nutrients or therapeutic agents, including total parenteral nutrition.

SUMMARY OF THE INVENTION

It is an object of the present invention to provide methods and apparatus for intravenous administration of nutrients or therapeutic agents, including total parenteral nutrition, that will substantially eliminate any risk of loss of blood through the catheter as well as problems resulting from the formation of blood clots inside or outside the catheter.

It is another object of the present invention to provide methods and apparatus for intravenous administration of nutrients and therapeutic agents, including total parenteral nutrition, which will reduce the incidence of infection in, on, or around the catheter.

It is another object of the present invention to provide methods and apparatus for administration of nutrients or therapeutic agents, including total parenteral nutrition, that will substantially reduce the risk of air embolism.

It is a further object of the present invention to provide methods and apparatus for intravenous administration of nutrients or therapeutic agents, including total parenteral nutrition, which do not require pumps and other complex flow control devices.

It is yet a further object of the present invention to provide methods and apparatus for intravenous administration of nutrients or therapeutic agents including total parenteral nutrition, such that any equipment used to insert the catheter, other than the catheter itself, can be easily and completely removed after insertion of the catheter.

It is another object of the present invention to allow intermittent temporary termination of intravenous therapy, including total parenteral nutrition, with disconnection from the source of intravenous therapy without the danger of catheter occlusion by blood clots and without the need for repeated flushing with heparin or other anticoagulant substances.

It is yet another object of the present invention to allow determination of the venous pressure, preferably in the superior vena cava (central venous pressure) of the vessel the catheter tip is positioned in without allowing blood reflux into the catheter and without the need for additional apparatus for manometers.

It is a further object of the present invention to allow easy subcutaneous passage of the catheter utilizing a passer which can be readily connected to the distal end of the catheter and used to simultaneously form a subcutaneous tunnel and thread the catheter therethrough.

According to the present invention the proximal end of a flexible catheter having a one way valve or valves adjacent its proximal end is inserted through the skin or through a surgical incision in the skin of a patient and into a vein having a suitably large blood flow therethrough. The catheter preferably has a coating of heparin or other anticoagulant substance on its internal and external surfaces, radiopaque markings and metric indicia, and a removable internal stiffener. The distal open end of the catheter has a male threaded fitting or coupler which is threadably coupled to a flow reducing adaptor which is, in turn, coupled to a source of intravenous fluid having the desired concentration of nutrients or therapeutic agents, via a standard intravenous drip connector. All extraneous apparatus necessary for the insertion of the catheter is easily removed after insertion. The intravenous solution flows by hydrostatic pressure through the catheter and into the vein, the maximum flow rate being limited to a safe level by the valve and by the flow reducing adaptor. The venous pressure inside the vein (venous pressure) is easily determined by finding the fluid pressure at which flow just stops and subtracting the opening pressure of the catheter valve or valves. The catheter may be intermittently disconnected from the source of intravenous fluids and capped without danger of blood clots forming in or on the catheter. A tubular passer can be readily connected to the male coupler at the distal end of the catheter and used to simultaneously form a subcutaneous tunnel and retrogradedly thread the catheter therethrough.

BRIEF DESCRIPTION OF THE DRAWINGS

FIG. 1A is a fragmentary view of the catheter forming a part of the short term intravenous therapy apparatus of the present invention. Shown in FIG. 1A are the removable internal stiffner and the threaded male coupler at the distal end of the catheter which threadably engages the flow reducing adaptor;

FIG. 1B is a fragmentary view of the catheter forming a part of the long term intravenous therapy apparatus of the present invention. The one way valve at the proximal end of the catheter is shown open or expanded which occurs when fluid inside of the catheter is at a pressure sufficiently greater than that outside of the catheter. Also shown in FIG. 1B is the cuff which surrounds the catheter and is imbedded in the subcutaneous tissue near the point where the catheter exits the body;

FIG. 2A shows the flow reducing adaptor which is threadably engaged with the male coupler at the distal end of the catheter. A cap may be screwed over the distal end of the adaptor to seal the same;

FIG. 2B shows the standard male fitting of an intravenous drip mechanism inserted into the distal end of the adaptor;

FIG. 3A shows a hypodermic needle and a sleeve which fits over the same, both forming part of the short term intravenous therapy apparatus. The hypodermic needle hub accepts the male fitting of a standard syringe;

FIG. 3B shows a fragmentary view of the catheter of FIG. 1A being guided through the sleeve of the short term intravenous therapy apparatus with the aid of the internal stiffner;

FIGS. 6A–6H are simplified anatomical views of a patient illustrating the manner in which the long term intravenous therapy or hyperalimentation apparatus is utilized.

DESCRIPTION OF THE PREFERRED EMBODIMENTS

Figure 4A:
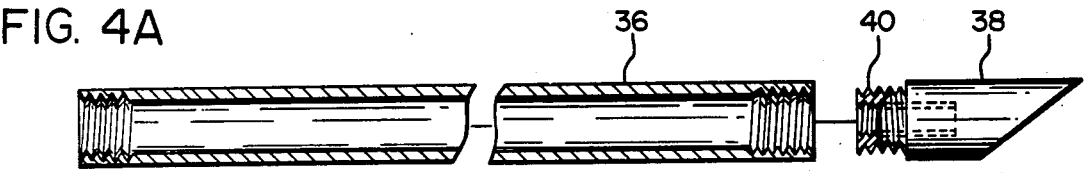
FIG. 4A shows a fragmentary view of the passer forming a part of the long term intravenous therapy apparatus.

The term 'proximal end' when used in reference to a needle, sleeve, or catheter, refers to the forward end thereof which is inserted into the patient's body. The term 'distal end' when used in reference to a needle, sleeve, or catheter, refers to the rearward end thereof which is situated externally of the patient's body.

According to the present invention, the apparatus utilized to perform short term intravenous therapy or hyperalimentation has certain mechanical elements in common with the apparatus utilized to perform long term intravenous therapy or hyperalimentation. Specifically, both preferably include a flexible catheter having a one way valve or valves adjacent its proximal end, internal and external coatings of heparin or other anticoagulant substance, radiopaque markings and metric indicia, a male threaded coupler at the distal end of the catheter, a removable internal stiffener, and a flow reducing adaptor which threadably engages the male coupler at the distal end of the catheter and which accepts the male fitting of a standard intravenous drip mechanism at its distal end, and may threadedly accept a cap at its distal end when intravenous therapy is temporarily interrupted. In addition, the short term intravenous therapy apparatus includes a syringe, needle, and external sleeve which are hereafter described. The long term apparatus includes a passer and a DACRON (trademark) cuff which is hereafter described.

Referring to FIG. 1A, the catheter 10 which is to be inserted into the patient is made of a durable, flexible, biocompatible material such as, but not necessarily, silicon rubber. One suitable material is sold under the registered trademark SILASTIC. Preferably the catheter is translucent so that the physician can determine the presence of air bubbles within the catheter. When used for short term intravenous therapy, the catheter preferably has sufficient length to extend from the skin of the patient to a vein which will not be adversely affected by the intravenous therapy or therapeutic agent administered. In the case of administration of concentrated hyperalimentation fluids, this lengths should be sufficient to extend from the site of insertion to the superior vena cava. The length will depend upon the size of the patient and the intended therapy to be administered. When used for long term intravenous therapy or hyperalimentation, the catheter preferably has sufficient length to extend from the superior vena cava to the deltopectoral groove or anterior lateral neck and further to a point midway down the anterior wall of the chest.

The catheter must have a relatively small outside diameter so that it can be readily inserted into a vein, such as the subclavian vein, without causing undo trauma to the vein and the surrounding tissues. Preferably the catheter has an outside diameter no greater than four millimeters. The inside diameter of the catheter must be large enough to permit intravenous solution to flow therethrough at a rate sufficient to allow the required amount of nutrients or therapeutic agents to be delivered. An example of a suitable size is an outside diameter of 2.2 mm and an inside diameter of 1.3 mm.

The catheter has a one way valve 12 (FIG. 1A) adjacent its proximal end. The valve may be formed by one or more individual slits precisely cut into the catheter wall. Multiple slits may be circumferentially spaced. As shown in FIG. 1B, the valve 12 opens when the fluid pressure inside the catheter is greater than the fluid pressure outside the catheter by a predetermined amount. The minimum amount of pressure needed to open the valve may be varied from catheter to catheter by varying the number of slits, length of the slits, the thickness of the catheter wall, or the elasticity of the catheter wall. A catheter with this type of one way valve will resist retrograde flow of fluids into the proximal end of the catheter. That is, when the hydrostatic pressure inside the catheter is greater than the pressure outside the catheter by a given amount, the opening(s) defined by the slit(s) 12 will expand (FIG. 1B), thereby allowing fluid to flow out of the catheter. However, when there is fluid pressure outside the proximal end of the catheter which is greater than the fluid pressure inside the catheter, the valve opening(s) will close and prevent retrograde flow into the catheter. One suitable catheter is the PUDENZ (trademark) cardiac catheter manufactured by Heyer Schulte, Inc., a subsidiary of American Hospital Supply Export Corporation. It is available in several different valve opening pressures.

The catheter preferably has a coating of anticoagulant substances, such as sodium heparin, on its internal and external surfaces to prevent the formation of blood clots thereon. The surfaces defined by the slit(s) 12 should preferably be coated in this manner to prevent blood clots from forming on the valve opening(s).

The proximal end 14 (FIG. 1A) is preferably pointed to facilitate insertion and advancement of the catheter in the vein. It may contain a quantity of radiopaque material 15, such a barium sulfate, so that the position of the proximal end of the catheter within the patient can be determined by x-ray. Alternatively, the entire catheter may be impregnated with a radiopaque material. The catheter preferably has indicia in the form of a metric scale which can be observed by the physician to determine the extent to which the catheter has been inserted.

The distal end of the catheter is open. An externally threaded, tubular male coupler 16 is tightly secured in the open distal end of the catheter. Preferably the coupler 16 is glued in place to prevent its accidental dislodgement. To facilitate insertion of the catheter into a vein a removable stiffener 18, such as a stainless steel wire, may be positioned in the catheter during insertion and removed through the open end of the catheter after the catheter is installed.

Referring to FIG. 2A, the coupler 16 is adapted to be threadably engaged with the internally threaded proximal female end of a tubular flow reducing adaptor 20. Adaptors with different flow reducing characteristics are available. The adaptor 22 has an internal fitting 21 with a small flow reducing orifice typically in the range of 16 to 27 gauge. The distal end of the adaptor 20 is fashioned to be coupled to the standard male fitting 22 (FIG. 2B) of an intravenous drip mechanism. The flow reducer is additionally threaded on its distal external surface so as to threadably accept a cap 24 (FIG. 2A) which may be utilized when no intravenous fluid therapy is being administered.

When the catheter is being used for long term therapy the intermediate section of the catheter may have a surrounding cuff 26 (FIG. 1B) made of a fabric material such as that sold under the registered trademark DACRON. As shown in FIGS. 6G and 6H the cuff 26 is placed on the long term catheter such that it will be located in the subcutaneous tissue under the skin where the catheter 10 exits from the body.

Figure 5A:
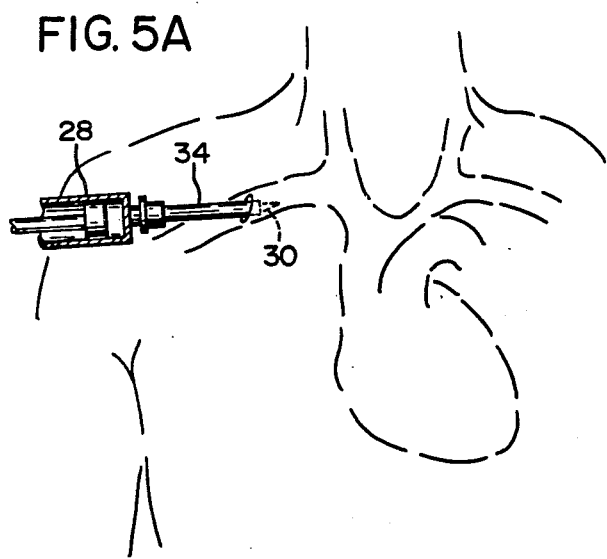
FIGS. 5A–5D are simplified anatomical views of a patient illustrating the manner in which the short term intravenous therapy or hyperalimentation apparatus is utilized.
Figure 5B:
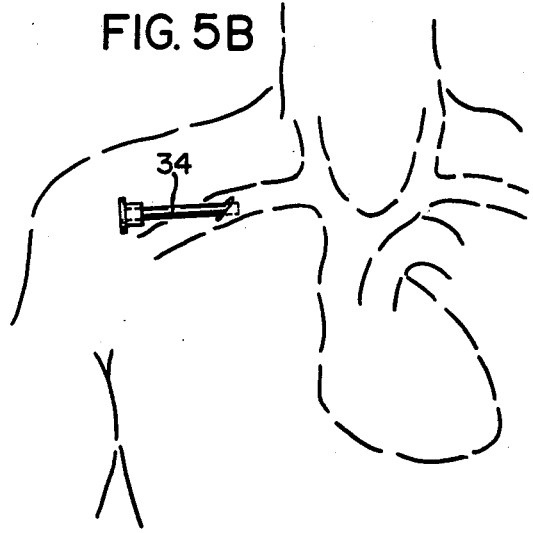
Figure 5C:
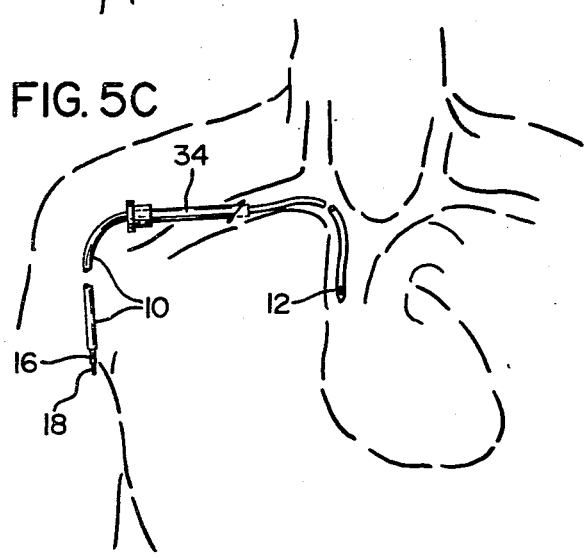

Referring to FIG. 3A, a standard syringe 28 has a needle 30 preferably with a coating 32 of TEFLON (trademark). A tubular sleeve 34 has an inside diameter slightly greater and a length slightly less than that of the coated needle. The sleeve can be slipped over the coated needle and the proximal end of the needle will be exposed (FIG. 5A). As shown in FIGS. 3B and 5C, the catheter 10 is guided through the sleeve 34 and into the vein with the aid of the internal stiffner 18.

Figure 4B:
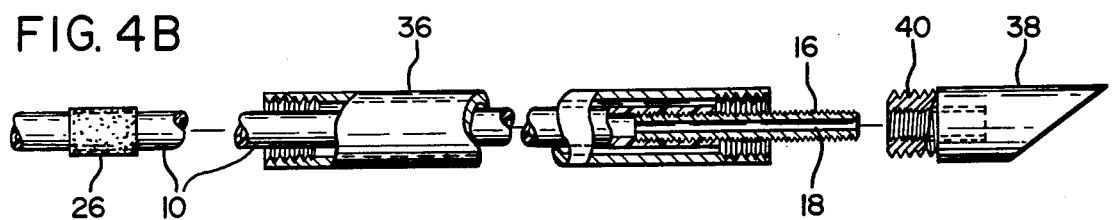
FIG. 4B shows the manner in which the passer of FIG. 4A is connected to the distal end of the catheter of FIG. 1B.

Referring to FIGS. 4A and 4B, the passer includes an elongate tube 36 adapted to slide over the male coupler 16 and the distal end of the catheter 10. The passer also has a tubular tip 38 having a sharp forward end. The rearward end of the tip has a cylindrical hub 40 with internal threading for threadedly engaging the male coupler 16 and external threads for threadedly engaging internal threads in either end of the tube 36.

When the catheter is to be installed on a short term basis, e.g., for a period of roughly three weeks or less, the following method may be utilized. A clearer understanding may be had by reference to FIGS. 5A–5D. With the patient in the lying position a vein which has been chosen in which to insert the catheter is dilated as much as possible, either by applying a proximal tourniquet or positioning the patient in a head down position so that the vein fills by hydrostatic pressure. Veins with a suitably large flow of blood therethrough and which are readily accessible include the cephalic, subclavian, internal jugular, external jugular, basilic, and median cubital veins. The skin over the vein is surgically prepared in the usual manner. Local anesthetic may be injected around the area of insertion.

Referring to FIG. 5A, the needle 30 fitted to the syringe 28 is inserted into the tubular sleeve 34. The proximal ends of the needle and sleeve are inserted through the skin and advanced until the proximal ends of the needle and sleeve enter the desired vein. The plunger of the syringe is slightly withdrawn. If blood is readily drawn into the syringe, the physician can be reasonably sure that the needle 30 are the sleeve 34 have entered the vein. The sleeve is then advanced slightly, held firmly, and the needle is withdrawn from the sleeve (FIG. 5B). The physician obstructs the distal end of the sleeve, e.g. with his or her finger, in order to stop the flow of blood therefrom. Prior to insertion of the catheter, which preferably has the internal stiffener 18 in place, it is filled with intravenous solution to eliminate air from its interior. The solution will not flow out the proximal end of the catheter through the one way valve 12 without a pressure head supplied by the solution in an IV bottle greater than the valve opening pressure. At this point the catheter is preferably not connected to the IV bottle.

Figure 5D:
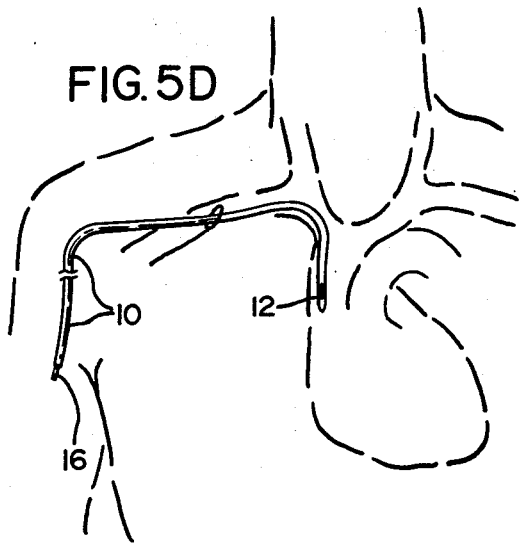

Referring to FIG. 5C, the proximal end of the catheter 10 is inserted through the sleeve 34 into the chosen vein, e.g. the subclavian, and advanced an appropriate distance as required by the type of intravenous fluids to be administered. Next, the sleeve 34 is slid out of the patient and over the distal end of the catheter (FIG. 5D). If an internal stiffener 18 had been used it is withdrawn at this time (FIG. 5D). The flow reducing adaptor 20 is then threadably secured to the threaded male coupler 16 at the distal end of the catheter (FIG. 6G–6H). The male fitting 22 of the IV drip mechanism is then secured to the distal end of the flow reducing adaptor 20 and the solution flows from the IV bottle solution through the drip mechanism, through the flow reducing adaptor, through the catheter, out the one way valve and into the vein.

It is also possible to insert the catheter into the patient without filling the catheter with intravenous solution before insertion. The one way valve at the catheter tip will remain closed during the insertion and prevent air from flowing through the catheter and causing an air embolism. Once the catheter is in place a syringe partially filled with intravenous solution may be used to aspirate air from the catheter. The catheter may be fully injected with the intravenous solution in the syringe prior to coupling the flow reducing adaptor to the drip mechanism and the bottle of intravenous solution.

When the catheter is in correct position it is secured to the skin near its point of insertion. This may be accomplished by sutures and/or bandages. Proper location of the proximal end of the catheter is preferably confirmed by x-ray.

When long term intravenous therapy or hyperalimentation is contemplated, e.g. for periods ranging from three weeks to several months or longer, the following method may be utilized. Referring to FIG. 6A, the patient is put in the supine position; the shoulder and desired catheter exit point prepared for surgical incision by shaving and scrubbing with antiseptic solutions. Sterile surgical drapes are applied to isolate the area of the deltopectoral groove and the desired catheter exit point. Local anesthetic is injected intradermally and subcutaneously in the area of the proposed incision, the path of the subcutaneous tunnel, and the proposed catheter exit site. An incision is made through the skin and the subcutaneous tissue dissected to reveal the cephalic vein. Again, other readily accessible veins, such as the jugulars or subclavian, which empty into the superior vena cava, may be utilized depending on circumstances.

Control of the vein is obtained by means of ligatures, clamps, or other means. The proximal end of the catheter is inserted into the vein such as the cephalic, either directly through an incision in the vein or via the hypodermic needle 30 and external sleeve 34 as previously described. The proximal end of the catheter, preferably with the internal stiffener 18 in place, is advanced into the superior vena cava. Proper location of the catheter is determined by x-ray as previously described. A ligature is tied around the cephalic or other vein distal to the point at which the catheter enters the vein. The internal stiffener, if present, is then removed (FIG. 6B). Another ligature is tied around the cephalic or other vein and catheter to anchor the position of the catheter in the vein.

Referring to FIG. 6C, the male coupler 16 at the distal end of the catheter is inserted through the tube 36 of the passer and is threadedly secured to the tip 38 of the passer. The tip is in turn threadedly secured to the distal end of the tube 36. Referring to FIGS. 6D and 6E, the physician grasps the passer and threads it subcutaneously from the incision in the shoulder to an exit point substantially midway down the anterior wall of the chest or some other selected location on the patient. The passer is guided through the skin at the exit point. The proximal portion of the catheter is firmly held at the incision in the shoulder while the passer is pulled to draw slack portions of the catheter through the subcutaneous tunnel. The passer, with catheter attached, is pulled until the cuff 26 of the catheter is located subcutaneously near the opening in the skin at the exit point.

Referring to FIG. 6F, the tip 38 of the passer is unscrewed from the tube 36 and from the male coupler 16. The tube 36 is slid off the catheter over its distal end (FIG. 6G). Air inside the catheter is aspirated with a syringe and the catheter is filled with an intravenous solution as previously described. The male coupler 16 is threadedly engaged with the flow reducing adaptor 20 which in turn is connected to the male fitting 22 of the drip mechanism coupled to the IV bottle. Alternatively, a cap 24 may threadedly engage the distal end of the flow reducing adaptor 20. The catheter is secured to the skin near the exit point with sutures and/or bandages. The incision in the shoulder is closed.

The intravenous nutrient or therapeutic solution flows by gravity from the solution bottle through the flow reducer and catheter and into the vein. The flow is driven by the hydrostatic pressure deriving from the position of the bottle of intravenous solution in relationship to the tip of the catheter within the patient. The maximum flow rate is restricted to a safe level by a flow reducing adaptor connected to the distal end of the catheter. Further control is provided by the specific opening pressure of the one way valve. When the bottle of intravenous solution is empty, there is no longer a pressure head sufficient to keep the one way valve open and thus the risk of air embolism is substantially eliminated. The one way valve at the proximal end of the catheter prevents retrograde flow of blood into the catheter and the problem of blood clotting in the catheter and thus stopping the intravenous solution flow is substantially eliminated. It is no longer necessary to have continuous flow of fluid through the catheter to prevent clot formation, nor is it necessary to periodically flush out the catheter with anticoagulant substances. This device thus eliminates the need for costly pumping and flow control devices and eliminates one of the major hazards of systems requiring such devices.

Even if the distal end of the catheter becomes uncoupled, the patient cannot lose blood through the catheter because the one way valve closes in the absence of internal fluid pressure. Furthermore, the risk of air embolism in such cases is minimal since air cannot travel through the closed end of the catheter without being under pressure.

The presence of an anticoagulant coating on the surface of the cather prevents the formation of blood clots on the inside or outside of the catheter which might impede intravenous solution flow, serve as a nidus of bacterial growth leading to bacterial septisemias, or serve as a source of septic emboli when the catheter is withdrawn.

It is easily possible to measure the patient's central venous pressure without allowing reflux of blood into the catheter and without the use of additional manometers or other equipment. This is done by determining the vertical distance between the fluid level in the bottle of intravenous solution and the proximal tip of the catheter at which flow through the catheter just stops or starts. The opening pressure, which is known, of the one way valve at the catheter tip is subtracted from this value to give the venous pressure outside the tip of the catheter. When the catheter tip is in the superior vena cava this value is the central venous pressure to a clinically accurate value.

The apparatus utilizes a minimum number of components. The sleeve of the short term catheter apparatus can be completely removed from the patient, thus reducing extraneous hardware and the hazards associated therewith. A passer can readily be coupled to the distal end of the long term catheter and allows for simultaneous subcutaneous tunneling and threading of the catheter to an exit site on the anterior chest wall.

The distal end of the long term catheter can be readily manipulated by the patient because of its convenient location, i.e., midway down the anterior wall of the chest or other suitable site. This arrangement is desirable because it allows the patient to self-administer nutrient or other therapeutic solutions on an intermittent basis.

As shown in FIG. 6H, upon completion of a particular infusion the catheter may be filled with an anticoagulant solution and the cap 24 threadedly connected to the distal end of the fluid flow reducing adaptor. The patient now has the freedom the ambulate without the constraint of an infusion apparatus connected to him/her. The patient may avoid prolonged hospitalization by conveniently self-administering nutrient or other therapeutic agents, including total parenteral nutrition, on an intermittent basis outside the hospital.

Having described the preferred embodiments of the invention, it will be apparent that the invention permits modification in arrangement and detail.

What is claimed is:

1. An apparatus for performing intravascular therapy including hyperalimentation comprising:
   a flexible catheter having a length sufficient to extend from a vessel in a patient having a suitably large flow of blood therethrough and through an exit site in the skin of the patient, the catheter having a valve adjacent its proximal end;
   a male coupler secured to the open distal end of the catheter; and
   a passer for threading the catheter subcutaneously, the passer including an elongate tube adapted to slide over the male coupler and the distal end of the catheter, a tip adapted to be releasably connected to the forward end of the tube, and means releasably to attach the distal end of the catheter to the tip.

2. An apparatus for performing intravascular therapy including hyperalimentation comprising:
   a flexible, closed-ended catheter having a length sufficient to extend from a vessel in a patient having a suitably large flow of blood therethrough and through an exit site in the skin of the patient,
   the catheter having a valve adjacent its proximal end;
   a coupler secured to the open distal end of the catheter;
   a passer for threading the catheter subcutaneously,
   the passer including an elongate tube adapted to slide over the male coupler and the distal end of the catheter,
   and a sharp edged tip adapted releasably to be connected to the male coupler and the forward end of the tube, for cutting a passageway through the body tissue of a patient to enable the passer to be passed subcutaneously beneath the skin of a patient whereby after emergence of the tip from the skin and removal of the tip from said tube, said catheter may be advanced within said tube, and said tube may be withdrawn from the body by sliding the same over said catheter leaving the catheter within the passageway formed by the passer beneath the skin of the patient.

3. The apparatus of claim 2 wherein said tip is threadedly engaged to said coupler and to said tube.

* * * * *